US011805769B2

United States Patent
Haff et al.

(10) Patent No.: US 11,805,769 B2
(45) Date of Patent: Nov. 7, 2023

(54) X-RAY INSECT IRRADIATOR

(71) Applicant: The United States of America, as represented by the Secretary of Agriculture, Washington, DC (US)

(72) Inventors: Ronald P. Haff, Albany, CA (US); Eric S. Jackson, Albany, CA (US); Robert M. Hnasko, Albany, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 342 days.

(21) Appl. No.: 16/883,221

(22) Filed: May 26, 2020

(65) Prior Publication Data

US 2021/0368767 A1    Dec. 2, 2021

(51) Int. Cl.
- *A01M 1/22* (2006.01)
- *A61L 2/08* (2006.01)
- *A61D 99/00* (2006.01)

(52) U.S. Cl.
CPC ............. *A01M 1/226* (2013.01); *A61L 2/082* (2013.01); *A01K 2227/706* (2013.01); *A61D 99/00* (2013.01)

(58) Field of Classification Search
CPC .. A01M 1/226; A61L 2/082; A01K 2227/706; A61D 99/00
See application file for complete search history.

(56) References Cited

U.S. PATENT DOCUMENTS

| | | | | |
|---|---|---|---|---|
| 3,604,181 A | * | 9/1971 | Adcox | B65B 5/061 53/531 |
| 4,368,690 A | * | 1/1983 | Tenzer | A01K 67/033 119/6.6 |
| 4,484,341 A | * | 11/1984 | Luniewski | B82Y 10/00 976/DIG. 444 |
| 6,690,020 B2 | * | 2/2004 | Loda | A61L 2/24 250/455.11 |
| 6,713,773 B1 | * | 3/2004 | Lyons | A23L 3/263 378/68 |
| 7,154,103 B2 | * | 12/2006 | Koenck | A23B 4/20 426/232 |
| 7,513,861 B2 | * | 4/2009 | Klein | A61N 5/1015 600/3 |
| 8,919,280 B1 | * | 12/2014 | Haff | A61D 1/00 119/6.5 |
| 10,159,229 B2 | * | 12/2018 | Marchant | F21V 7/22 |
| 2004/0052702 A1 | * | 3/2004 | Shuman | A23L 3/003 422/208 |
| 2004/0231229 A1 | * | 11/2004 | Lenker | A01M 1/02 43/107 |

\* cited by examiner

*Primary Examiner* — Tien Q Dinh
*Assistant Examiner* — Kevin M Dennis
(74) *Attorney, Agent, or Firm* — John Fado; Robert Jones

(57) ABSTRACT

Packages of insects are attached to a carrier cylinder and the cylinder is rotated in a radiation field so that the packaged insects are sterilized. The radiation field is created by a plurality of x-ray tubes mounted above the carrier cylinder. The tubes (and their respective radiation sources) are positioned so that a consistent radiation dosage is delivered at the surface of the cylinder—thereby imparting both a precise and uniform dose of radiation to the insect packages affixed to the surface of the cylinder.

14 Claims, 8 Drawing Sheets

X-RAY INSECT IRRADIATOR

FIELD OF THE INVENTION

The disclosed subject matter relates to treating insect-sized objects with radiation. Specifically, the invention relates to irradiating insects so that the insects survive the treatment and receive a consistent and effective dose of radiation and consequently are incapable of reproduction (i.e. sterilized).

BACKGROUND OF THE INVENTION

The sterile insect technique (SIT) is a method of biological insect control, whereby large numbers of a targeted pests are sterilized through a treatment process that exposes the living insects to a relatively low but effective dosage of radiation. After exposure, the treated insects are released into the wild. The treated and released insects are usually male because (among other things) the females may cause damage by laying eggs in the crop, or, in the case of mosquitoes, taking blood from humans.

The sterile males compete with wild males to mate with the females. Females that mate with a sterile male produce no offspring, thus reducing the next generation's population. Sterile insects are not self-replicating and, therefore cannot become established in the environment. Repeated release of sterile males over low population densities can further reduce and (in cases of isolation) eventually eliminate pest populations.

The technique has been successfully used to eradicate the screw-worm fly (*Cochliomyia hominivorax*) from North and Central America. The technique has also been used to successfully control fruit fly pests, particularly the Mediterranean fruit fly (*Ceratitis capitata*) and the Mexican fruit fly (*Anastrepha ludens*). Active research is being conducted to determine this technique's effectiveness in combatting the Queensland Fruit Fly (*Bactrocera tyroni*).

Current insect irradiation methods generally comprise placing multiple live insects in large cannisters and irradiating the cannisters with a gamma radiation source. However, due to attenuation of the radiation as it penetrates the cannister, this process frequently results in a non-uniform dose distribution and subsequent overdosing and killing or disabling insects in the outer circumference of the canister while the insects near the center may not be effectively sterilized.

Obtaining and maintaining radiation sources has become increasingly difficult and expensive. Reasons include increasing government regulation and restriction due to Homeland Security concerns, radioisotope suppliers going out of business, and the general aging and subsequent weakening of existing sources. Alternatives to gamma radiation sources are urgently needed.

The need exists for an insect sterilizing system that delivers a consistent and effective non-gamma radiation dose to irradiated insects. The current system comprises a cost-effective means of irradiating large numbers of insects with a uniform and consistent dosage of radiation without killing or damaging the insects. The current process uses x-ray tubes (rather than gamma ray-producing radioisotopes) as a radiation source. Each x-ray tube radiates x-rays from a specific internal point, generally known as the target, through a metal plate, generally known as the window (hereafter referred to as the x-ray source, or just source) to the exterior. The x-ray tubes are placed at specifically calculated positions/distances to deliver a precise and uniform radiation dose to all insects.

SUMMARY OF THE INVENTION

This disclosure is directed to a system for irradiating insects (or alternatively, insect-sized samples). In the preferred embodiment, the system comprises x-ray sources mounted above a rotating carrier cylinder. The distance above the surface of the cylinder and the spacing between the x-ray sources is precisely determined so that the radiation dose along a designated irradiation line on the surface of the cylinder remains constant. This configuration allows for both precise and uniform dosing of packages of live insects that are attached to the cylinder surface—as the packages repeatedly pass through the irradiation line.

Note that mechanisms in some of the FIGs. may contain multiple examples of essentially the same component. For simplicity and clarity, only a small number of the exemplary components may be identified with a reference number. Unless otherwise specified, other non-referenced components with essentially the same structure as the exemplary component should be considered to be identified by the same reference number as the exemplary component.

DETAILED DESCRIPTION OF PREFERRED EMBODIMENTS

Figure 1:
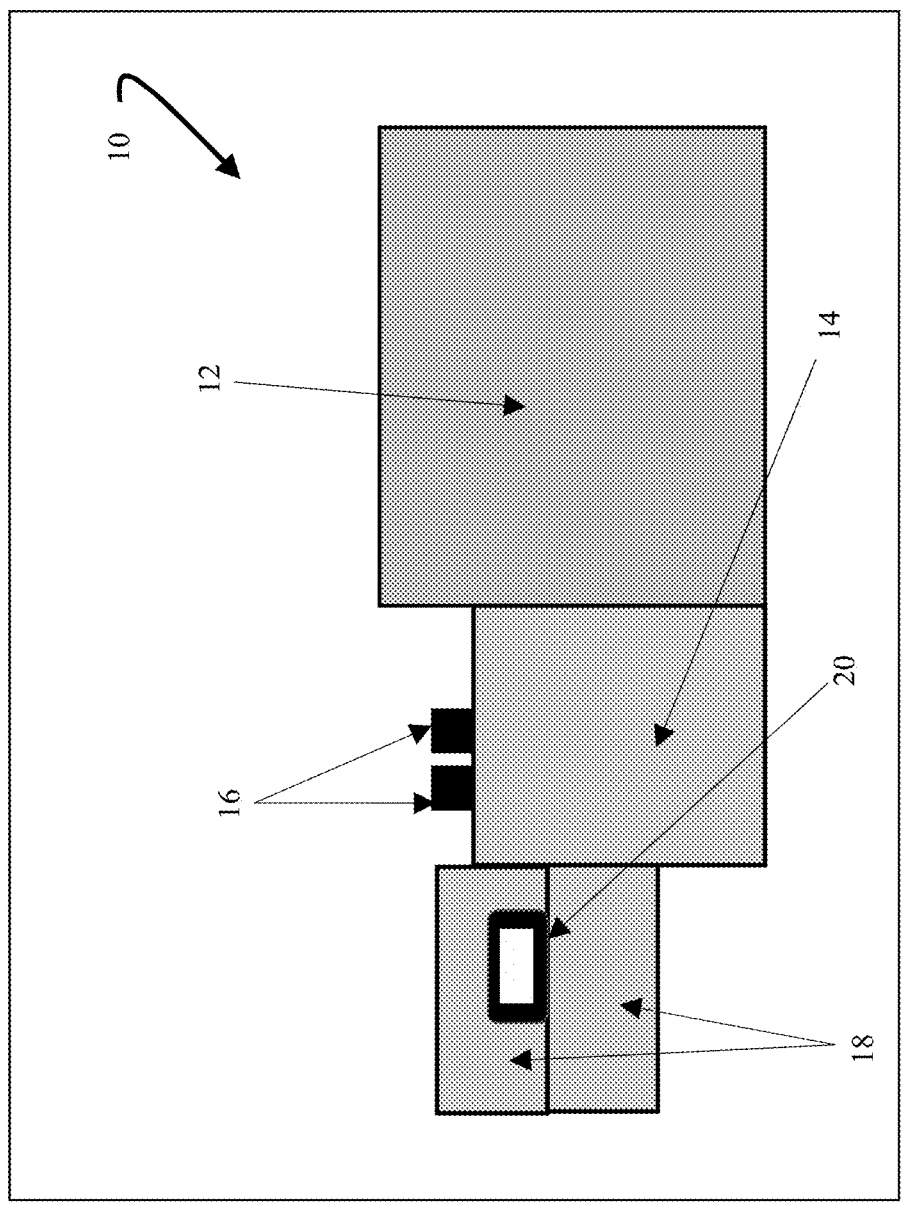
FIG. 1 is a photograph of a device/equipment embodying the current system.

As generally shown in FIG. 1, the insect irradiation system 10 comprises a shielded cabinet 12 that houses the primary operational components of the system 10. A chiller 14 is positioned adjacent to the cabinet 12 to cool the x-ray tubes 27 (see FIG. 2) within the cabinet 10, and at least one Geiger counter 16 is also positioned adjacent the cabinet 12 to detect any radioactivity present outside the cabinet 12. Power supplies 18 provide high voltage (100 kV) electrical power to the x-ray tubes 27. An ion chamber-based probe 36 (see FIG. 2) inside the cabinet 12 provides input to a radiation dose measuring system 20, thereby allowing real-time monitoring of the x-ray dose.

Figure 2:
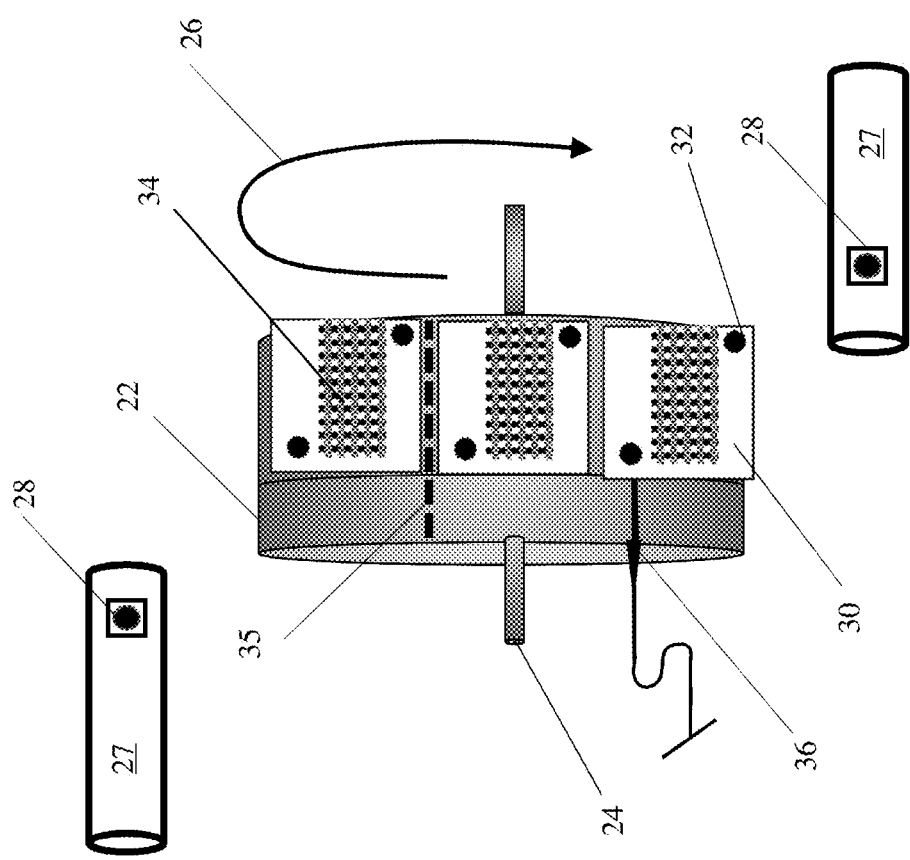
FIG. 2 is a schematic view of selected components of the preferred embodiment of the current system.

FIG. 2 shows the primary operational components of the preferred embodiment of the system 10 that are housed within the x-ray cabinet 12 shown in FIG. 1. In accordance with the preferred embodiment, a centrally positioned carrier cylinder 22 rotates about a center axel 24 in the direction of the arrow 26. Although FIG. 2 shows the carrier cylinder 22 rotating counterclockwise, the direction of rotation is not critical/significant. The carrier cylinder 22 rotates in a radiation field created by at least two x-ray tubes 27 and their respective sources 28 that are located at specifically calculated positions relative to the carrier cylinder 22—resulting in a uniform radiation dose distribution along a virtual (projected) linear area across the cylinder 22 surface. For the purposes of this disclosure, this linear area is designated as an "irradiation line" 35. The position of the irradiation line remains constant even as the surface of the cylinder rotates i.e. the irradiation line does not rotate with the cylinder.

As noted above, the current process uses x-ray tubes 27 (rather than gamma ray-producing radioisotopes) to generate radiation. Each x-ray tube 27 radiates x-rays from a specific internal point, generally known as the "target", through a metal plate, generally known as the "window". In this disclosure, the window is referred to as the "x-ray source" 28. Note that the x-ray tubes 27 and the x-ray source 28 are represented schematically in the current figures. The actual shape and size of the components may vary significantly, however all functional configurations should be considered within the scope of the current system 10.

The intensity of the electromagnetic radiation (and therefore the radiation dose) declines/attenuates by a factor of the square of the distance traversed by the x-rays. Thus, along a surface line between two or more radiation sources (the irradiation line), the total dose delivered at any point is the sum of doses from each source 28. Moving between x-ray sources, the dose will decrease from one source 28 while increasing from another. Thus, ideal locations can be calculated in terms of the height of the sources 28 above the cylinder 22 surface, and the distance between sources 28 that results in a (near) uniform dose distribution across the surface of a cylinder 22.

In the preferred embodiment, the x-ray tubes 27 are model CXR-105 (Comet, Inc.), with a maximum output of 100 keV, and 10 mA (1000 W). X-rays are emitted from a metallic "target" through an x-ray window which is approximated as the radiation point source 28.

As shown in FIG. 2, a plurality of sealable container packages 30 (such as ZIPLOC™ bags) may be removably attached to an outer surface of the cylinder 22 by a hook and loop-type attachment system 32 (such as VELCRO™ tape). In alternative embodiments, the packages 30 and means of attachment may comprise any configuration, system, or method known in the art. In the preferred embodiment, the sealable packages 30 contain live insects 34 (or other similarly sized products).

An ion chamber probe 36 is also attached to an outer surface of the cylinder 22. The probe 36 is in communication with the radiation measurement system 20 (see FIG. 1) which provides a digital readout of the accumulated radiation dose. The probe 36 may communicate with the monitoring system through either a wired or wireless connection.

In the preferred embodiment, as the cylinder 22 rotates, a system operator observes the monitor 20 and terminates the process when the accumulated radiation dose reaches a previously established threshold/targeted dose. The established target dose varies based on the anatomy and characteristics of the insects (or other irradiated products). In alternative embodiments, the process may be partially or fully automated so that a controller terminates the process when a targeted radiation dose is achieved.

The design of the current system is based on the following set of algorithms:

$$\text{For } 0 < p < x_1: I(p) = H^2 \left[ \frac{1}{H^2 + (x_1 - p)^2} + \frac{1}{H^2 + (x_2 - p)^2} \right]$$

$$\text{For } x_1 < p < x_2: I(p) = H^2 \left[ \frac{1}{H^2 + (p - x_1)^2} + \frac{1}{H^2 + (x_2 - p)^2} \right]$$

$$\text{For } p > x_2: I(p) = H^2 \left[ \frac{1}{H^2 + (p - x_1)^2} + \frac{1}{H^2 + (p - x_2)^2} \right]$$

The algorithms describe the mathematical relationship between the intensity of a radiation dose (I); the position (p) where the dose is measured (the irradiation line), and; the location of two x-ray sources relative to the position (p).

Figure 3:
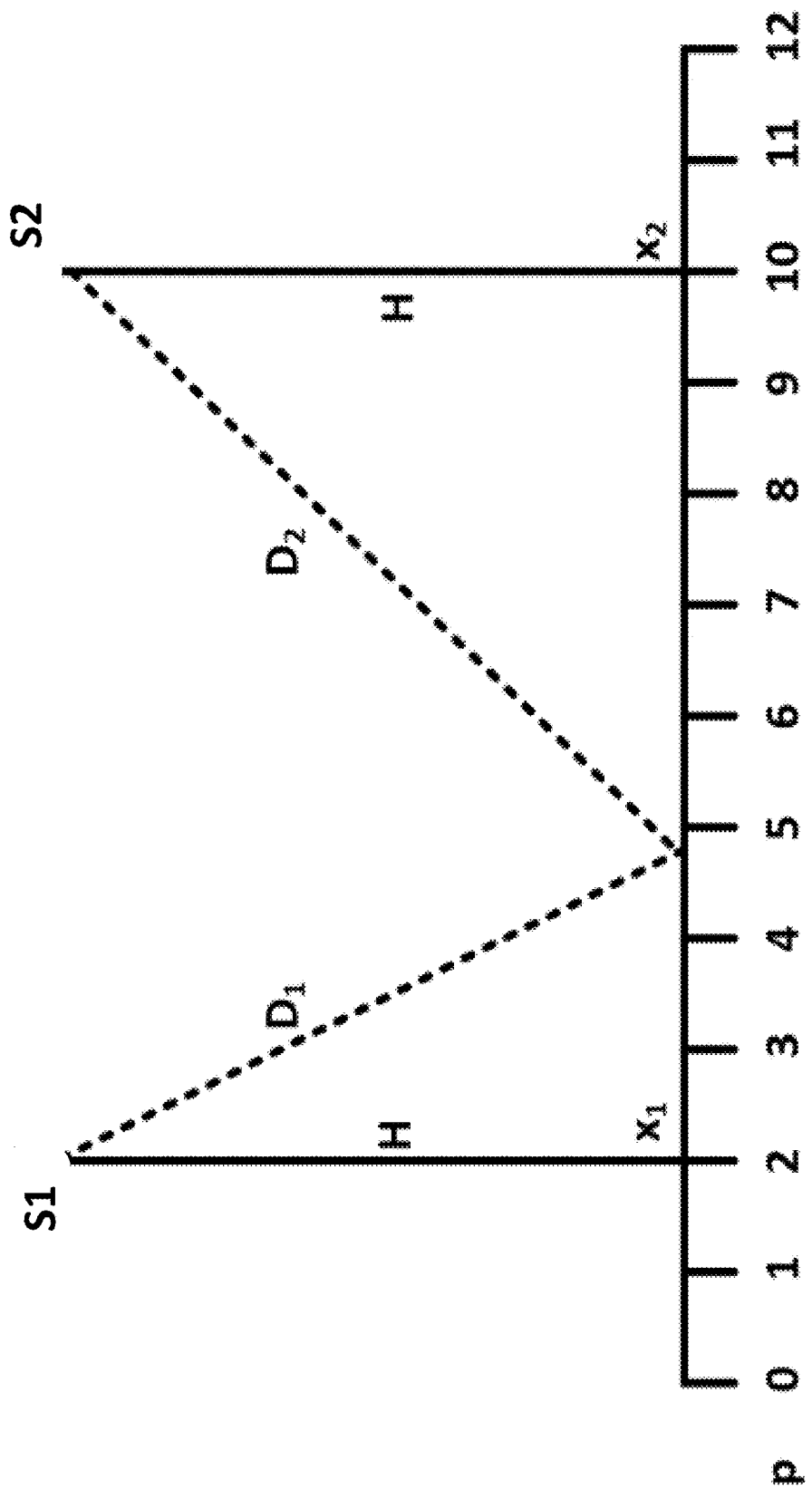
FIG. 3 is a plot showing the graphical elements of the algorithms used by the inventors.

FIG. 3 shows the (graphically represented) relative relationships between the components of the system, as described in the algorithms. As shown in FIG. 3, the distances ($D_1$, $D_2$) from the radiation sources ($S_1$ and $S_2$) to the irradiated object are a function of the vertical height (H) of the sources above the irradiated object. The horizontal distances ($x_1$, $x_2$) represent the relative horizontal locations of the radiation sources. Based on the $1/D^2$ attenuation of electromagnetic radiation reflected in the above algorithms, the inventors calculated the expected x-ray intensity (i.e. dose, (I)) as a percentage of the dose at a point (p) on the irradiation line.

Figure 4:
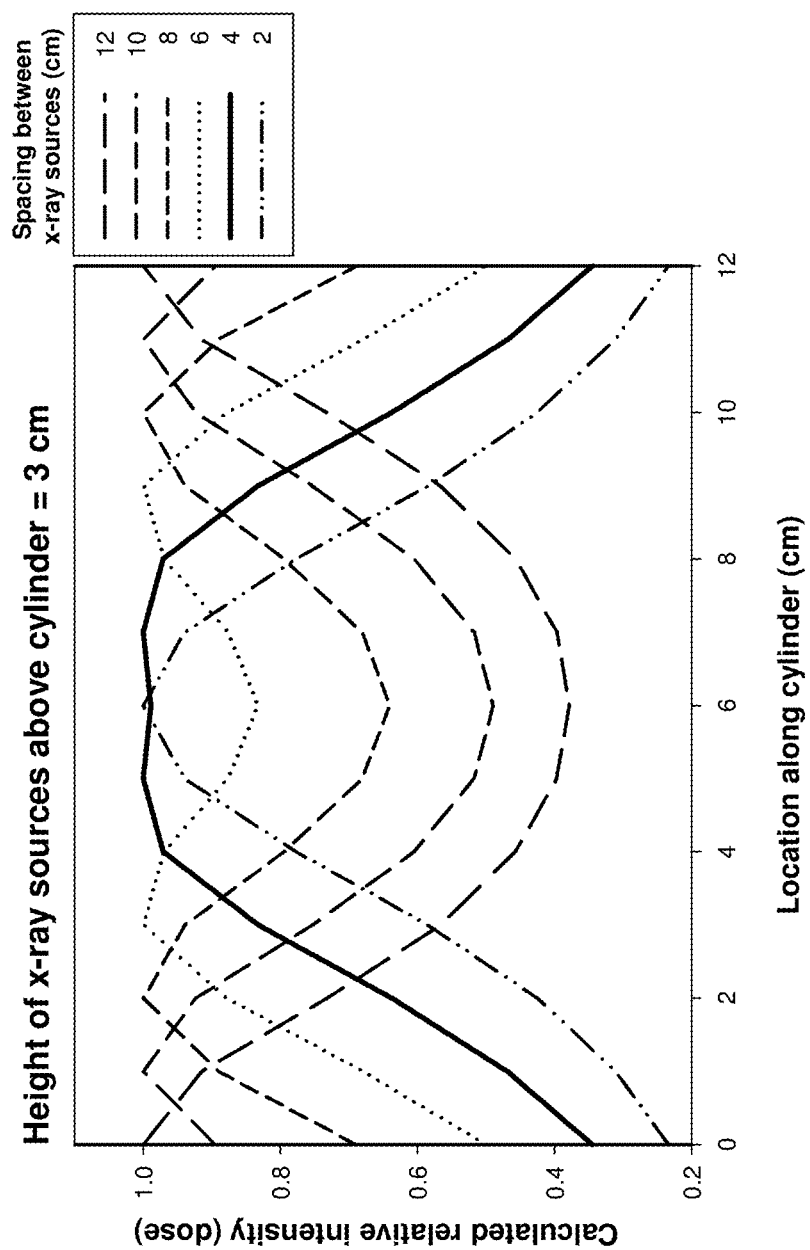
FIG. 4 shows the expected distribution of radiation dose delivered on the surface of the carrier cylinder 22 when two x-ray sources 28 are positioned at a height of 3 cm above the surface of the carrier cylinder 22 (see FIG. 2) for different x-ray source spacing distances.
Figure 5:
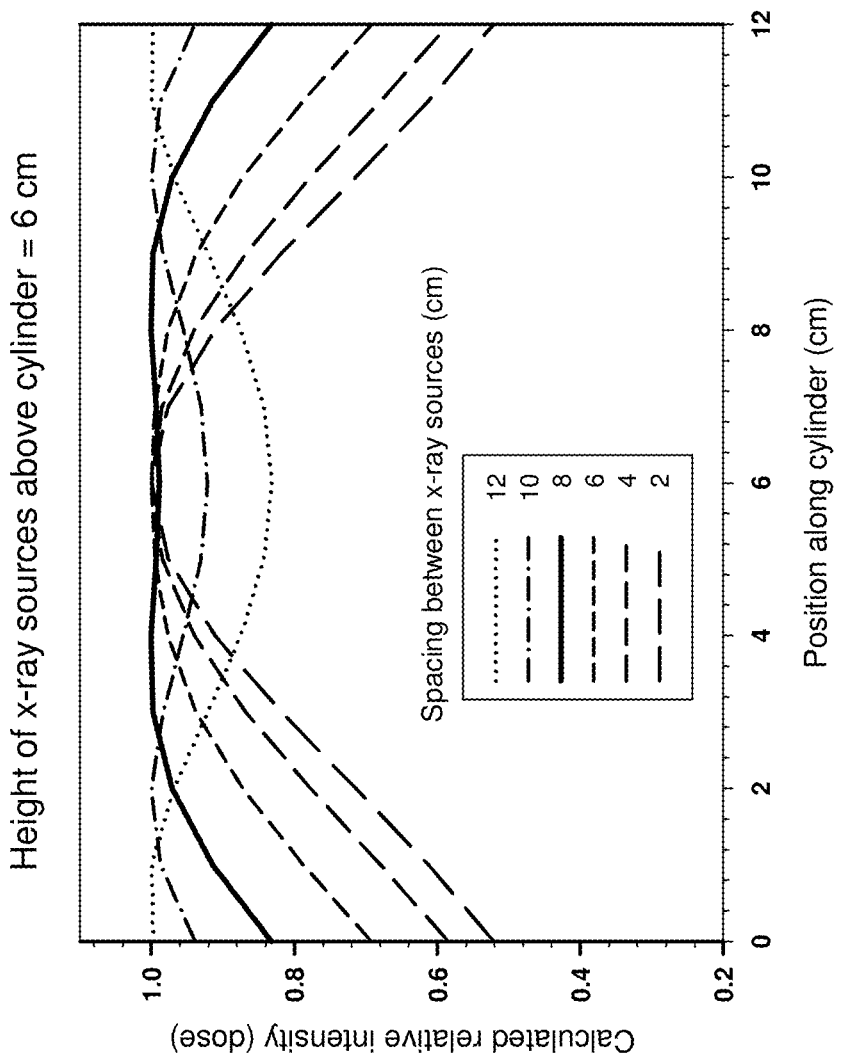
FIG. 5 shows the expected distribution of radiation dose delivered on the surface of the carrier cylinder 22 when two x-ray sources 28 are positioned at a height of 6 cm above the surface of the carrier cylinder 22 (see FIG. 2) for different x-ray source spacing distances.

The inventors used the above algorithms to calculate the $x_1$, $x_2$, and H values that generate the most uniform dose along the radiation line 35. This objective was accomplished by solving the equations numerically, i.e. plotting results for different values of the parameters. The plots shown are for two sources at a height H of three cm (FIG. 4) and six cm (FIG. 5) above the carrier cylinder 22 surface, and various locations of $x_1$ and $x_2$ which corresponds to different spacing between the x-ray sources 28.

In particular, with H=6 cm and x-ray sources spaced 8 cm apart ($x_1$=2, $x_2$=10) high uniformity of dose is observed. Since electromagnetic radiation loses intensity over distance in a predictable fashion, x-ray sources can be strategically situated in relation to both each other, and the area to be irradiated so as to achieve a uniform intensity (i.e. dose). However, in operation, the radiation dose is affected by multiple factors in addition to electromagnetic radiation attenuation over distance. Actual measurements of the dose distribution must be made for each particular configuration and adjustments made by trial and error to fine-tune the system for best results.

In the current configuration, samples to be irradiated (i.e. sealable container packages 30 of live insects 34) are attached to the cylinder 22 surface, which is rotated so that the samples/packages 30 repeatedly pass through the irradiation line 35, thereby accumulating a radiation dose with each revolution. Since the dose is (nearly) uniform along the irradiation line, all insects in the sample packages 30 ultimately receive a consistent high precision dose. The ion probe 36 attached to the surface of the cylinder 22 measures the accumulated radiation dose in real-time. When the desired dose is achieved, the operator shuts down the x-ray sources 28.

Figure 6:
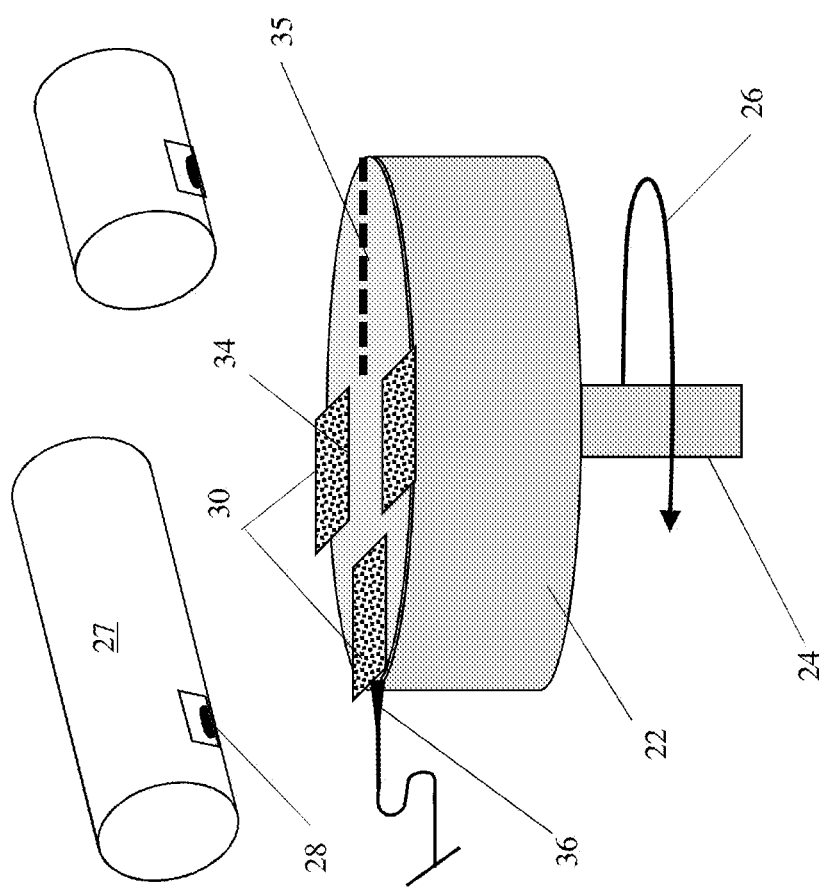
FIG. 6 shows an alternative embodiment of the current invention.

FIG. 6 shows an alternative embodiment of the current system. In accordance with the alternative embodiment, a vertically extending carrier cylinder 22 rotates about a center axel 24 in a horizontal plane in the direction of the arrow 26. In this embodiment, the top portion of cylinder 22 has a horizontal planar surface. The carrier cylinder 22 rotates in a radiation field created by at least two x-ray tubes 27 and their respective sources 28 that are located at specifically calculated positions relative to the carrier cylinder 22—resulting in a uniform radiation dose distribution across the cylinder 22 surface along an irradiation line 35. In this embodiment, the irradiation line extends perpendicular to the axis of rotation.

As shown in FIG. 6, a plurality of sealable container packages 30 containing live insects 34 (or other similarly sized products) may be removably attached to the top planar surface of the cylinder 22. An ion chamber probe 36 is attached to the top surface of the cylinder 22. The probe 36 is in communication with the radiation measurement system 20 (see FIG. 1) which provides a digital readout of the accumulated radiation dose. As the cylinder 22 rotates, a system operator observes the monitor 20 and terminates the process when the accumulated radiation dose reaches a previously established threshold/targeted dose. The established target dose and containment package/system 30 varies based on the anatomy and characteristics of the insects (or other products).

Figure 7:
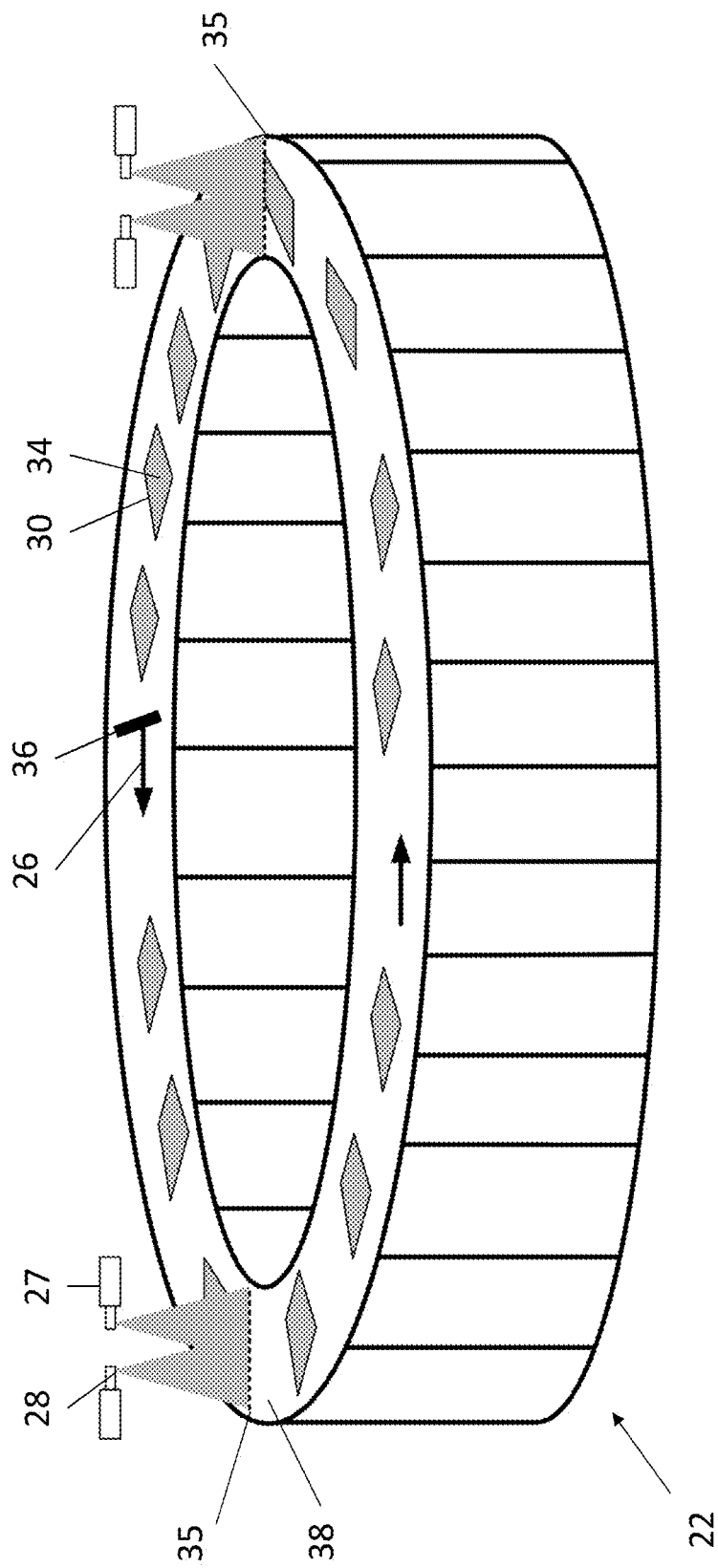
FIG. 7 shows a further alternative embodiment of the current invention.

The alternative embodiment shown in FIG. 7 is a special case of the embodiment shown in FIG. 6. In the FIG. 7 embodiment the top planar surface of the carrier cylinder 22 is scaled up to be a circular carousel conveyor system with multiple irradiation lines 35. In this embodiment, it is important to ensure that the probe 36 completes the same number of revolutions on the conveyor system 38 as each of the sealable packages 30 since the distance travelled and thus the received dose is much greater per cycle.

Figure 8:
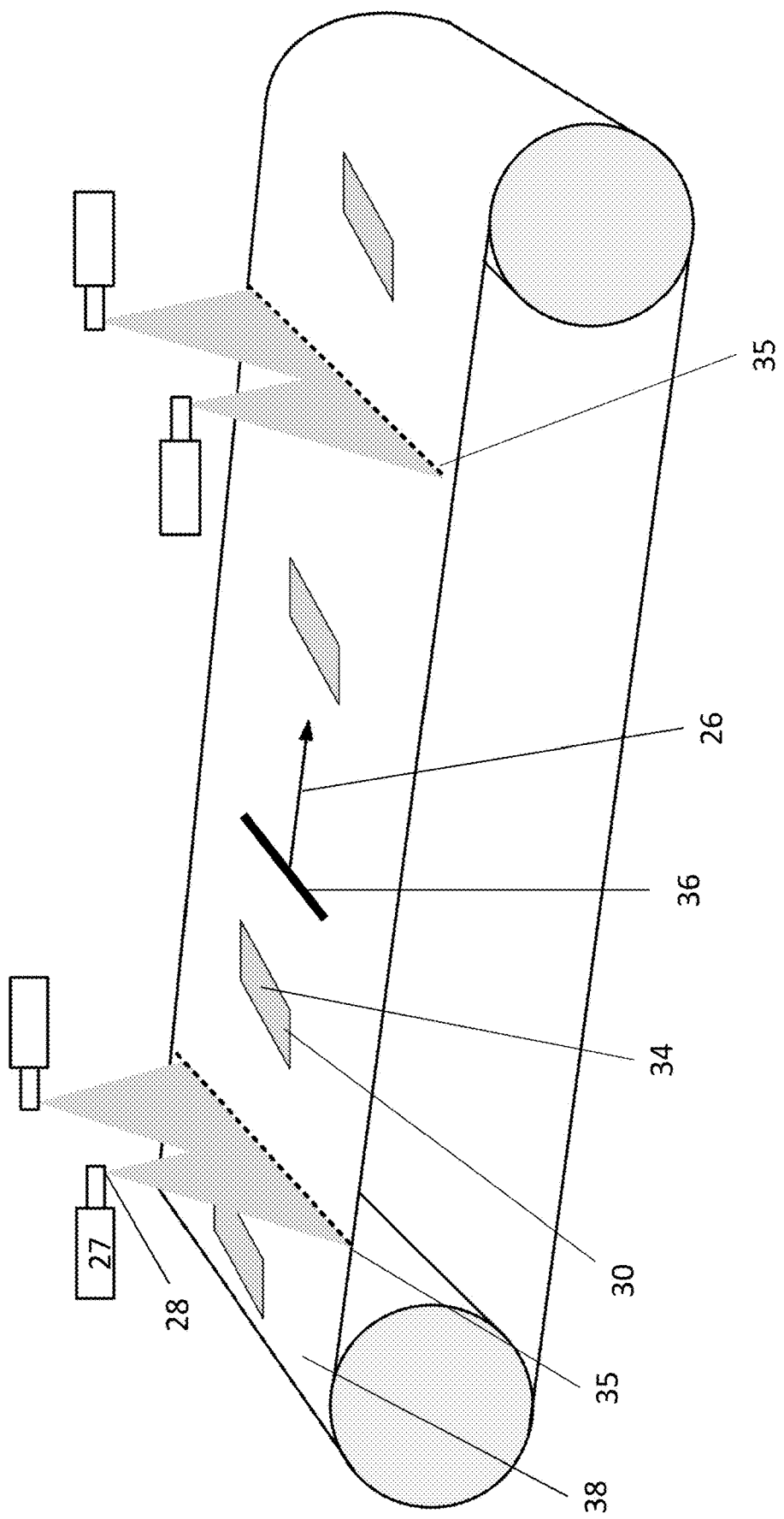
FIG. 8 shows an additional alternative embodiment of the current invention.

FIG. 8 shows a further alternative embodiment. In the FIG. 8 embodiment a conveyor system 38 moves sealable packages 30 containing live insects 34 (or other similarly sized products) in the direction of the arrows 26. The conveyor system 38 may comprise a belt-type system or may comprise multiple individual rotating powered rollers/cylinders (not shown) that propel packages 30 down the conveyor system 38. The packages 30 are moved through a radiation field created by at least two x-ray tubes 27 and their respective sources 28. The radiation sources 28 are positioned at specifically calculated positions relative to the packages 30—resulting in a uniform radiation dose distribution across irradiation 35 lines on the conveyor 38. In this alternative embodiment, more than two x-ray tubes 27/sources 28 could generate multiple irradiation lines 35 in order to deliver increased radiation dose.

In the FIG. 8 alternative embodiment, the sealable packages 30 conveying the live insects 34 do not travel repeatedly through the conveyor system 38, but rather start at one end and travel to the other. Therefore, in this embodiment, the ion probe 36 is used separately to measure the dose received for a single pass from beginning to end of the conveyor system 38. The received dose for a single pass is at least partially dependent on the speed of the conveyor, and thus the appropriate conveyor system 38 speed can be determined to deliver a predetermined dose uniformly to all treated insects 34 as they traverse the system 38. Thus, once the ion probe is used to determine the appropriate belt speed for a required x-ray dose then it is no longer required during the irradiation process. The established target dose varies based on the anatomy and characteristics of the insects (or other products) in the package 30.

For the foregoing reasons, it is clear that the subject matter described herein provides an innovative system for irradiating insects. The current system may be modified in multiple ways and applied in various technological applications. For example, although the described embodiments are directed to irradiating insects, irradiating other similar-sized objects should be considered within the scope of the invention. The disclosed method and apparatus may be modified and customized as required by a specific operation or application, and the individual components may be modified and defined, as required, to achieve the desired result.

Although the materials of construction are not described, they may include a variety of compositions consistent with the function described herein. Such variations are not to be regarded as a departure from the spirit and scope of this disclosure, and all such modifications as would be obvious to one skilled in the art are intended to be included within the scope of the following claims.

The amounts, percentages and ranges disclosed herein are not meant to be limiting, and increments between the recited amounts, percentages and ranges are specifically envisioned as part of the invention. All ranges and parameters disclosed herein are understood to encompass any and all sub-ranges subsumed therein, and every number between the endpoints. For example, a stated range of "1 to 10" should be considered to include any and all sub-ranges between (and inclusive of) the minimum value of 1 and the maximum value of 10 including all integer values and decimal values; that is, all sub-ranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Similarly, if the term "about" precedes a numerically quantifiable measurement, that measurement is assumed to vary by as much as 10%. Essentially, as used herein, the term "about" refers to a quantity, level, value, or amount that varies by as much 10% to a reference quantity, level, value, or amount.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein). The invention illustratively disclosed herein suitably may be practiced in the absence of any element which is not specifically disclosed herein.

What is claimed is:

1. A system for irradiating insects, the system comprising:
   at least two radiation sources;
   a rotating cylinder, the at least two radiation sources being positioned adjacent to the rotating cylinder;
   a non-rotating irradiation line, the non-rotating irradiation line comprising a uniform radiation dose linear area on an outer surface of the rotating cylinder, the non-rotating irradiation line being projected by the at least two radiation sources, the at least two radiation sources being strategically spaced to project a uniform radiation dose along the non-rotating irradiation line;

at least one package of insects attached to the outer surface of the rotating cylinder so that as the cylinder rotates, the uniform radiation dose is applied to the at least one package of insects each time the at least one package of insects passes through the non-rotating irradiation line; and, a dosimetry probe attached to the outer surface of the rotating cylinder rotating with the at least one package of insects;

wherein the system is structured so that the rotating dosimetry probe communicates the radiation dose received by the at least one package of insects to an electronic display that is monitored by an operator or an automated controller, whereby system operations are terminated when a desired radiation dose is reached.

2. The system of claim 1 wherein the system is structured so that the insects in the system are alive and fertile at a beginning of irradiation, and alive and infertile after the irradiation.

3. The system of claim 1 wherein the rotating cylinder comprises a horizontally extending rotating cylinder so that the irradiation line extends parallel with the axis of rotation of the rotating cylinder.

4. The system of claim 3 wherein the at least one package of insects is attached to rounded sides of the rotating cylinder.

5. The system of claim 1 wherein the rotating cylinder comprises a vertically extending rotating cylinder, the irradiation line extending perpendicular and outward from the axis of rotation to an outer circumference of the rotating cylinder.

6. The system of claim 1 wherein the rotating cylinder comprises a vertically extending cylinder, the top of the rotating cylinder having a planar surface.

7. The system of claim 1 wherein the rotating cylinder comprises a vertically extending rotating cylinder, the top of the rotating cylinder having a planar surface, the at least one package of insects is attached to the planar top portion of the rotating cylinder.

8. The system of claim 1 wherein the system is enclosed in a radiation containment cabinet.

9. The system of claim 8 wherein the radiation sources are cooled by a coolant system positioned adjacent to the radiation containment cabinet.

10. The system of claim 1 wherein the system comprises a carousel-type conveying system configured so that the insects are conveyed on a circular path.

11. The system of claim 1 wherein the surface comprises a surface on a linear conveying system, the insects being irradiated as the insects are conveyed past the at least two radiation sources.

12. The system of claim 11 wherein the conveyor is configured so that the at least one package of insects is deposited at one end of the linear conveying system, and packages of irradiated insects are removed from an opposite end of the linear conveying system.

13. The system of claim 11 wherein at least two sets of the at least two radiation sources irradiate the insects.

14. A method of sterilizing insects, the method comprising:
(a) supplying the system of claim 1 and packages of the insects; and
(b) operating the system so that the insects in the packages are irradiated and thereby sterilized.

* * * * *